(12) United States Patent
Nygaard et al.

(10) Patent No.: US 8,175,697 B2
(45) Date of Patent: May 8, 2012

(54) CATHETER FOR INSERTION INTO THE HUMAN BODY

(75) Inventors: Per Ehrenreich Nygaard, Søborg (DK); Tommy Bjørn Olsen, Frederikssund (DK); Niels Henrik Lange, Humlebæk (DK)

(73) Assignee: B-K Medical A/S, Herlev (DK)

( * ) Notice: Subject to any disclaimer, the term of this patent is extended or adjusted under 35 U.S.C. 154(b) by 1096 days.

(21) Appl. No.: 10/672,520

(22) Filed: Sep. 25, 2003

(65) Prior Publication Data

US 2005/0020938 A1    Jan. 27, 2005

(30) Foreign Application Priority Data

Sep. 25, 2002 (DK) ................................. 2002 01419

(51) Int. Cl.
*A61N 1/30* (2006.01)
(52) U.S. Cl. .............................. 604/20; 604/22; 600/437
(58) Field of Classification Search .................... 604/22, 604/20; 600/562, 437, 439, 585
See application file for complete search history.

(56) References Cited

U.S. PATENT DOCUMENTS

| 4,542,747 | A | | 9/1985 | Zurinski et al. | 128/660 |
|---|---|---|---|---|---|
| 5,931,787 | A | * | 8/1999 | Dietz et al. | 600/461 |
| 5,954,637 | A | * | 9/1999 | Francis | 600/138 |
| 6,524,251 | B2 | * | 2/2003 | Rabiner et al. | 600/439 |

* cited by examiner

*Primary Examiner* — Kevin C Sirmons
*Assistant Examiner* — Deanna K Hall
(74) *Attorney, Agent, or Firm* — Cooper & Dunham LLP

(57) ABSTRACT

A catheter for insertion into the human body and which includes one or more optionally scanning ultrasonic transducers (7) and a needle guide, which can be operated from the outside and used for collecting tissue samples from the human body. The catheter includes two substantially semicircular parts (2, 3), where a rod (4) is inserted between said parts and at the end is provided with an ultrasonic transducer (7), said two semicircular parts (2, 3) being kept together by means of an outer tube (5) passed over the two semicircular parts (2, 3), and where the surface of one semicircular part (2) is provided with a longitudinal groove (6) for the insertion of a flexible needle (12) for the extraction of tissue samples. The resulting catheter is very user-friendly and easy to disassemble for disinfecting and sterilizing purposes.

4 Claims, 5 Drawing Sheets

CATHETER FOR INSERTION INTO THE HUMAN BODY

TECHNICAL FIELD

The invention relates to a catheter for insertion into the human body and which includes one or more optionally scanning ultrasonic transducers as well as a surgical instrument to be operated from the outside.

BACKGROUND OF ART

Many catheters are known for insertion into the human body in order to extract tissue samples. Many of these known catheters are encumbered with the draw-back that they are difficult to clean and disinfect upon use.

According to Danish Patent Application No. 12/98 attempts have been made at solving this problem by forming the needle guide separately relative to the remaining part of the catheter which has been coated with a sterile sheath. Then the needle guide is secured to the remaining part of the catheter on the outer side of the sheath in such a manner that the needle need not penetrate said sheath during a sampling. As a result it is not necessary to disinfect the catheter upon use. However, great interest attaches in avoiding such a sheath.

DISCLOSURE OF THE INVENTION

The object of the invention is therefore to provide a catheter of the above type which is easier to disinfect than hitherto known and which therefore does not need such a sheath.

A catheter of the above type is according to the invention characterised in that it includes one or more parts of a substantially completely circular or partially circular cross section, where a rod is inserted between said parts and at the end is provided with an ultrasonic transducer, said completely or partially circular parts being surrounded by an outer tube passed over the completely or partially circular parts, and where the surface of at least one of the completely or partially circular parts is provided with a longitudinal groove for the insertion of the surgical instrument.

As a result, the catheter includes only very few parts which in the separated state are easy to clean and disinfect.

Moreover, the surgical instrument may according to the invention be formed by a flexible needle for the insertion of a substance or for the extraction of tissue samples.

In addition, the longitudinal groove in the surface of the circular part may according to the invention be longer than the surrounding outer tube.

Furthermore, the longitudinal groove in the surface of the circular part may according to the invention be formed such that the flexible needle is positioned immediately behind the outer tube, preferably by said groove in the surface of the circular part ending in the surface of said circular part immediately behind said outer surrounding tube.

BRIEF DESCRIPTION OF THE DRAWINGS

The invention is explained in detail below with reference to the drawings, in which.

BEST MODE FOR CARRYING OUT THE INVENTION

Figure 1:
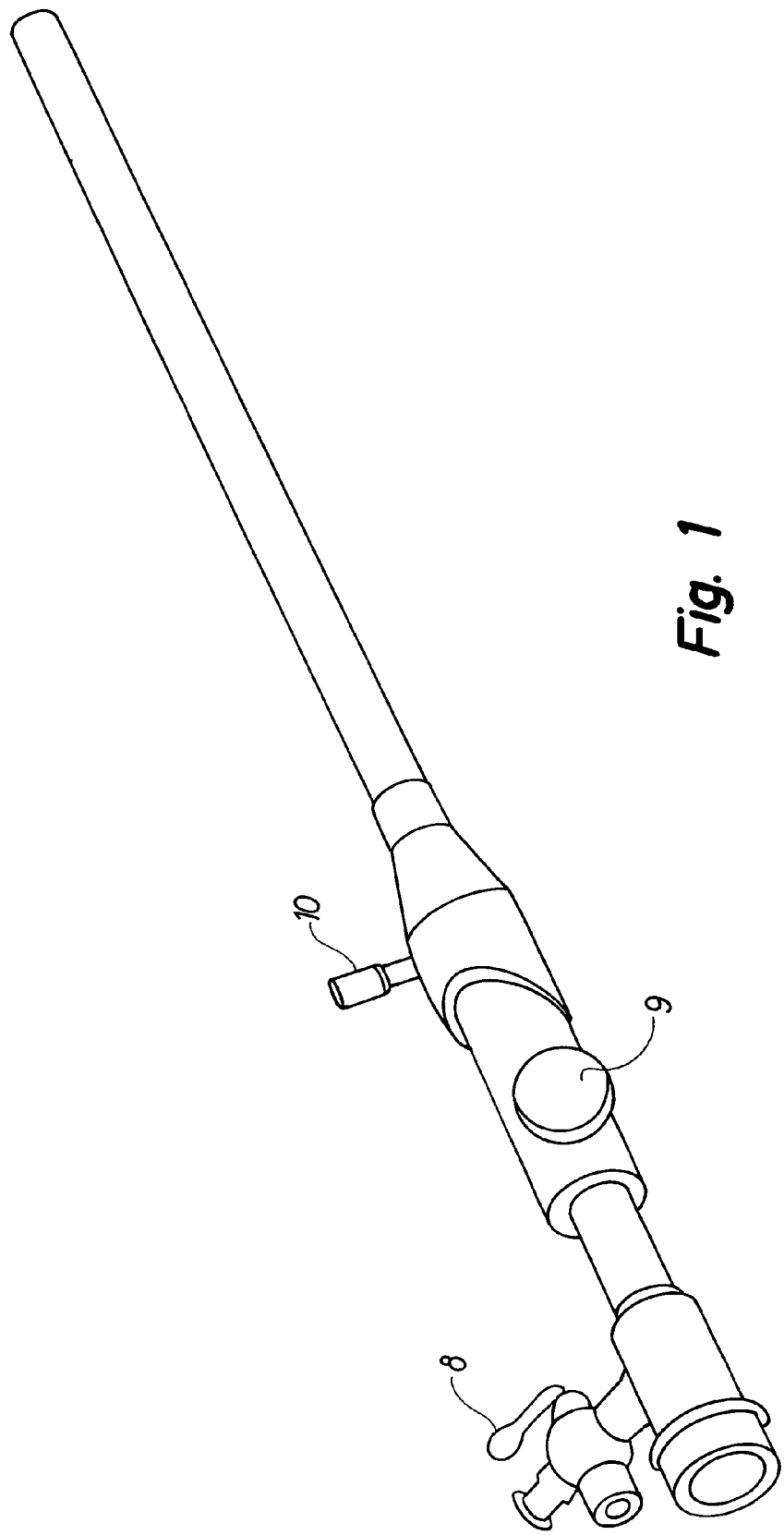
FIG. 1 shows a catheter according to the invention which includes two parts of a semicircular cross section which are kept together by means of an outer tube.
Figure 2:
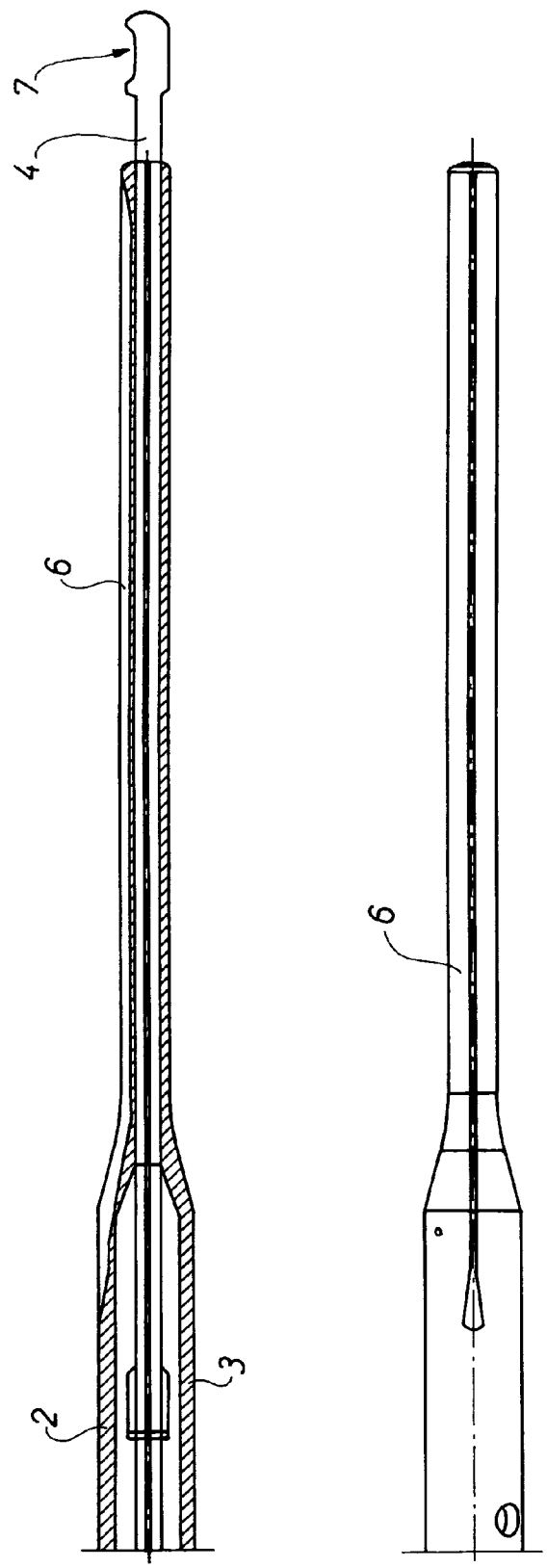
FIG. 2 is a longitudinal sectional view from the outside of the two parts of a semicircular cross section.
Figure 3:
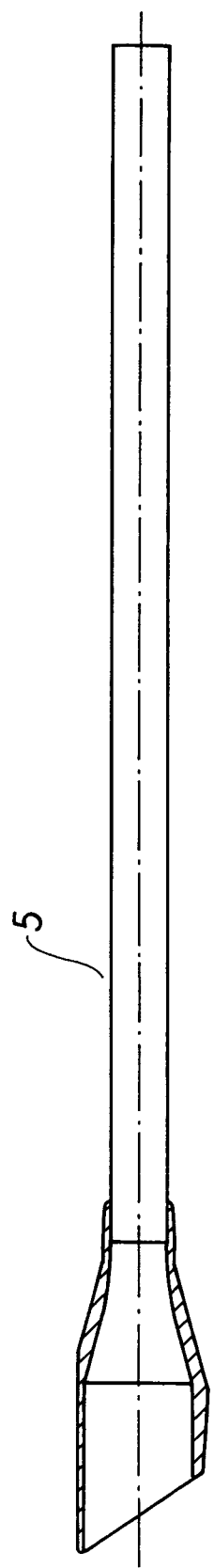
FIG. 3 shows the outer tube.
Figure 4:
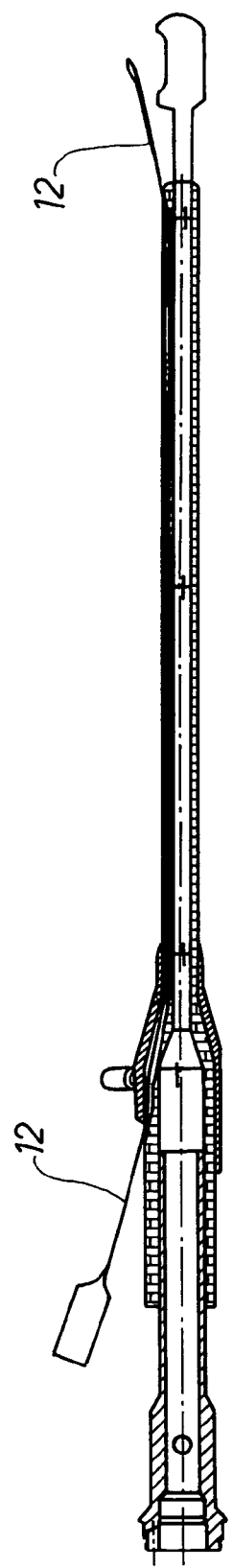
FIG. 4 shows a catheter housing a surgical instrument in form of a needle for the introduction of a substance or for the extraction of a tissue sample.

FIG. 1 shows a catheter according to the invention for insertion into the human body. The catheter includes one or more parts 2, 3 of a substantially completely or partially circular cross section, said parts preferably being two substantially semicircular parts. A rod 4 is inserted between these parts 2, 3, said rod being provided at the projecting end with an ultrasonic transducer 7. The rod 4 can be rotated relative to the two semicircular parts 2, 3. The two semicircular parts 2, 3 are kept together by means of an outer tube 5 passed over said two semicircular parts 2, 3. The abutting surfaces of the two semicircular parts are formed such that they lock relative to one another. A longitudinal groove 6 is provided in the surface of at least one semicircular part 2, said groove allowing the insertion of a surgical instrument, such as a flexible needle or a cannula 12 for a sampling or for the introduction of a substance. The groove 6 is longer than the outer tube 5 and shaped such that the cannula 12 is positioned so as to extend immediately behind the outer tube 5, said groove 6 ending in the surface of the circular part 2 immediately behind the outer tube 5. During the extraction of a tissue or liquid sample from the human body the cannula 12 can then be observed by means of the ultrasonic transducer 7 in form of the location where said cannula 12 passes the transverse plane being scanned by said transducer 7. The observation can for instance be displayed on a screen.

The catheter is furthermore equipped with a valve 8 for the introduction of a liquid, preferably brine. The brine exits at the opposite end where the needle 12 extends out of the catheter in such a manner that an acoustic impedance matching always applies to the tissue to be examined.

In addition, means 9 can be provided for fixing the rod 4 relative to the two semicircular parts 2, 3, as well as a screw 10 can be provided for securing the outer tube 5 relative to the semicircular parts 2, 3.

The catheter can for instance be used for rectal purposes, such as in connection with rectoscopy.

The catheter is made of stainless steel and presents an outside diameter of approximately 6 to 24 mm.

The catheter can optionally be made of plastics or a combination of stainless steel and plastics.

In addition, the catheter is very user-friendly as well as easy to disassemble for disinfecting and sterilising purposes.

Figure 5:
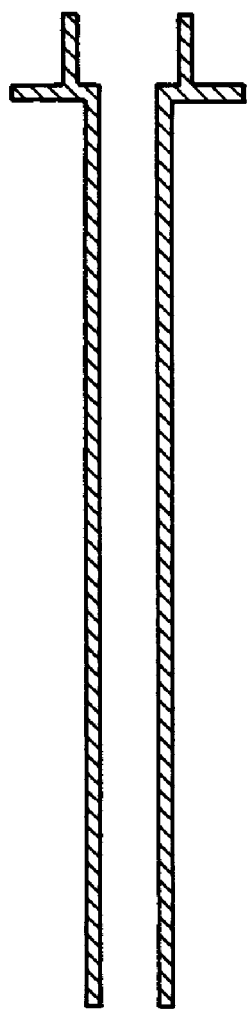
FIG. 5 shows a sigmoidoscope.

Another embodiment, a so-called sigmoidoscope or a rectoscope, includes a plastic or steel tube, cf. FIG. 5. The plastic tube is then used as light conductor which renders it possible to introduce a telescope into the plastic tube which then exposes the surrounding tissue. It is possible to insert a cannula for a sampling in the rim of the above plastic tube. The catheter according to the invention can optionally be inserted in the above plastic tube upon detection of the various internal organs by means of the telescope.

Figure 6:
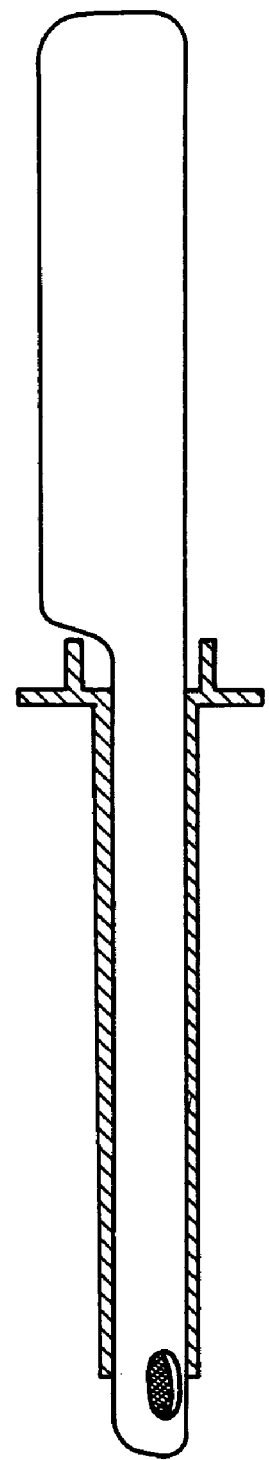
FIG. 6 shows a second embodiment of the catheter.

FIG. 6 shows another embodiment of the catheter, said embodiment being introduced into the sigmoidoscope shown in FIG. 5.

The invention claimed is:

1. A catheter for insertion into a human body comprising one or more scanning-enabled ultrasonic transducers as well as a surgical instrument, wherein the surgical instrument is configured to be operated from the outside of the human body and comprises a needle configured for the introduction of a substance or for the extraction of tissue samples,
- wherein the catheter comprises at least two inner parts having substantially circular arc cross sections, and wherein a rod is inserted between said inner parts and at the end of the rod is provided with at least one scanning-enabled ultrasonic transducer,
  - said inner parts being enclosed in an outer tube which passes over the inner parts, and
- wherein the outer surface of at least one of the inner parts is provided with a longitudinal groove configured to provide an opening for insertion of the needle,
- wherein the inner parts removably engage each other and are bound by said outer tube when the catheter is assembled,
- wherein the inner parts have abutting surfaces shaped so that they can be locked relative to one another, forming a longitudinal seam between the inner parts,
  - the inner parts capable of being removed from the outer tube and disengaged from each other,
and
- wherein the longitudinal groove is shaped such that the needle can be inserted from the outside of the human body into the human body via the longitudinal groove.

2. A catheter according to claim 1, wherein a bottom surface of the groove gradually slopes toward the outer surface of the inner part at an end of said inner part intended for insertion into the human body.

3. A catheter according to claim 1, wherein the rod with the ultrasonic transducer can be rotated relative to the inner parts.

4. A catheter for insertion into the human body comprising one or more scanning-enabled ultrasonic transducers as well as a surgical instrument to be operated from outside the human body, said catheter comprising:
- a pair of substantially hemicylindrical shell parts, the hemicylindrical shell parts removably engageable with each other;
- a rod inserted between said hemicylindrical shell parts, an end of the rod provided with an ultrasonic transducer; and
- an outer tube passing over and holding the hemicylindrical shell parts together, wherein an outer surface of at least one of the hemicylindrical shell parts is provided with a longitudinal groove for insertion of the surgical instrument,
  - the pair of hemicylindrical shell parts capable of being removed from the outer tube and disengaged from each other,
- wherein the surgical instrument comprises a needle for the introduction of a substance or for the extraction of tissue samples, and
- wherein the longitudinal groove is shaped such that the surgical instrument can be inserted from the outside of the human body into the human body via the longitudinal groove.

* * * * *